United States Patent
Xu et al.

(10) Patent No.: US 11,060,041 B2
(45) Date of Patent: Jul. 13, 2021

(54) HYDROTHERMAL LIQUEFACTION OF LIGNOCELLULOSIC BIOMASS TO BIO-OILS WITH CONTROLLED MOLECULAR WEIGHTS

(71) Applicant: THE UNIVERSITY OF WESTERN ONTARIO, London (CA)

(72) Inventors: Chunbao Xu, London (CA); Zhongshun Yuan, London (CA); Shanghuan Feng, Ilderton (CA)

(73) Assignee: THE UNIVERSITY OF WESTERN ONTARIO, London (CA)

( * ) Notice: Subject to any disclaimer, the term of this patent is extended or adjusted under 35 U.S.C. 154(b) by 202 days.

(21) Appl. No.: 16/310,889

(22) PCT Filed: Jun. 27, 2017

(86) PCT No.: PCT/CA2017/050774
§ 371 (c)(1),
(2) Date: Dec. 18, 2018

(87) PCT Pub. No.: WO2017/219151
PCT Pub. Date: Dec. 28, 2017

(65) Prior Publication Data
US 2020/0308500 A1 Oct. 1, 2020

Related U.S. Application Data

(60) Provisional application No. 62/354,332, filed on Jun. 24, 2016.

(51) Int. Cl.
*C10L 1/02* (2006.01)
*C07C 29/80* (2006.01)
(Continued)

(52) U.S. Cl.
CPC .............. *C10L 1/02* (2013.01); *C07C 29/80* (2013.01); *C07C 37/685* (2013.01); *C07C 37/74* (2013.01);
(Continued)

(58) Field of Classification Search
CPC ............... C10L 1/02; C10L 2290/08; C10L 2200/0484; C10L 2290/06; C10L 2290/543; C07C 29/80; C07C 37/685; C07C 37/74
See application file for complete search history.

(56) References Cited

U.S. PATENT DOCUMENTS 4,935,567 A   6/1990  Yokoyama et al.
7,276,148 B2 * 10/2007  Plopski .................. C02F 11/10
                                              208/117
(Continued)

FOREIGN PATENT DOCUMENTS

CA      2397338        7/2016
CN   104449790 A       3/2015
ES      2412241        7/2018

OTHER PUBLICATIONS

Zhang et al 2010: Zhang LH, Xu CB, Champagne P. Overview of recent advances in thermochemical conversion of biomass. Energy Convers Manage, 2010; 51: 969-82.
(Continued)

*Primary Examiner* — Cephia D Toomer
(74) *Attorney, Agent, or Firm* — Hill & Schumacher

(57) ABSTRACT

The disclosed invention is a process for liquefaction of hydrolysis residue of lignocellulosic biomass, original lignocellulosic biomass or municipal solid waste in alcohol-water media at alkaline conditions, for the production of low-$M_w$ bio-oils. The disclosed process is characterized in that it works for the direct liquefaction of the biomass, and operates under mild conditions (<300° C. and <10 MPa) employ-
(Continued)

Liquefaction process ing alkali compounds as catalysts (NaOH, KOH, CaO, $Na_2CO_3$, $K_2CO_3$, $Ca(OH)_2$ or $Ba(OH)_2$). The process is further characterized in that it employs mixed solvents (glycerol-water, ethylene-glycol, water, glycerol-alcohol-water or ethylene-glycol-alcohol water), where all solvents are recyclable and reusable. The low-Mw bio-oils from hydrolysis residue of lignocellulosic biomass, original lignocellulosic biomass or municipal solid waste can be utilized as a liquid bio-fuel or bio-based chemicals for the production of various bio-based materials.

22 Claims, 1 Drawing Sheet

(51) Int. Cl.
C07C 37/68 (2006.01)
C07C 37/74 (2006.01)
(52) U.S. Cl.
CPC ... C10L 2200/0484 (2013.01); C10L 2290/06 (2013.01); C10L 2290/08 (2013.01); C10L 2290/543 (2013.01)

(56) References Cited

U.S. PATENT DOCUMENTS

| | | | | |
|---|---|---|---|---|
| 7,473,285 | B2* | 1/2009 | Russell | B01J 3/008 44/605 |
| 7,753,969 | B2* | 7/2010 | Stiller | C10L 1/00 44/307 |
| 2011/0180752 | A1* | 7/2011 | Zhu | C10L 1/023 252/182.31 |

OTHER PUBLICATIONS

Toor et al 2011: Toor SS, Rosendahl L, Rudolf A. Hydrothermal liquefaction of biomass: a review of subcritical water technologies. Energy 2011, 36, 2328-42.
Demirbas 2000: Demirbas, A. Mechanisms of liquefaction and pyrolysis reactions of biomass. Energy Convers Manage 2000, 41,633-46.
Demirbas 2011: Demirbas, A. Biomass Resource Facilities and Biomass Conversion Processing for Fuels and Chemicals. Energy Convers Manage 2001, 42, 1357-78.
Liu and Zhang 2008: Liu ZG, Zhang FS. Effects of various solvents on the liquefaction of biomass to produce fuels and chemical feedstocks. Energy Convers Manage 2008, 49, 3498-504.
Karagoz et al 2005: Karagoz S, Bhaskar T, Muto A, Sakata Y. Comparative studies of oil compositions produced from sawdust, rice husk, lignin and cellulose by hydrothermal treatment. Fuel 2005;84:875-84.
Peterson et al 2008: Peterson AA, Vogel F, Lachance RP, Froling M, Antal JMJ, Tester JW. Thermochemical biofuel production in hydrothermal media: A review of sub- and supercritical water technologies. Energy Environ Sci 2008, 1, 32-65.

Kang et al 2013: Kang SM, Li XL, Fan J, Chang J. Hydrothermal conversion of lignin: A review. Renew Sustain Energy Rev 2013, 27, 546-58.
Akhtar and Admin 2011: Akhtar J, Amin NAS. A review on process conditions for optimum bio-oil yield in hydrothermal liquefaction of biomass. Renew Sustain Energy Rev, 2011, 15, 1615-24.
Behrendt et al 2008: Behrendt F, Neubauer Y, Oevermann M, Wilmes B, Zobel N. Direct Liquefaction of Biomass. Chem Eng Technol, 2008, 31, 667-77.
Tekin and Karagoz 2013: Tekin K, Karagoz S. Non-catalytic and catalytic hydrothermal liquefaction of biomass. Res Chem Intermed, 2013, 39,485-98.
Pavlovic et al 2013: Pavlovic I, Knez Z, Skerget M. Hydrothermal reactions of agricultural and food processing wastes in sub- and supercritical water: a review of fundamentals, mechanisms, and state of research. J Agric Food Chem 2013, 61, 8003-25.
Ruiz et al 2013: Ruiz HA, Rodriguez-Jasso RM, Fernandes BD, Vicente AA, Teixeira JA. Hydrothermal processing, as an alternative for upgrading agriculture residues and marine biomass according to the biorefinery concept: A review. Renew Sustain Energy Rev 2013, 21, 35-51.
Knez et al 2015: Knez Z, Markocic E, Hrncic MK, Ravber M, Skerget M. High pressure water reforming of biomass for energy and chemicals: A short review. J Supercrit Fluid 2015, 96, 46-52.
Xu and Lad 2007: Xu C*, Lad N, 2007. Production of Heavy Oils with High Caloric Values by Direct Liquefaction of Woody Biomass in Sub/Near-critical Water. Energy Fuels, 22, 635-642.
Xu and Etcheverry 2008: Xu C*, Etcheverry T, 2008. Hydro-liquefaction of woody biomass in sub- and super-critical ethanol with iron-based catalysts. Fuel, 87, 335-345.
Xu and Lancaster 2008: Xu C*, Lancaster J, 2008. Conversion of secondary pulp/paper sludge to bio-oils by direct liquefaction in hot compressed or sub- and near-critical water. Water Research 42, 1571-1582.
Yang et al 2009: Yang Y, Gilbert A, Xu C*, 2009. Production of bio-crude from forestry.
Li et al 2011: Li H, Hurley S, Xu C*, 2011. Liquefactions of peat to bio-crude in supercritical water with a novel iron catalyst. Fuel, 90: 412-420.
Zhang et al 2011: Zhang L, Champagne P*, Xu C*, 2011. Bio-crude production from secondary pulp/paper-mill sludge and waste newspaper via co-liquefaction in hot-compressed water. Energy, 36: 2142-2150.
Feng et al 2013: Feng, S., Z. Yuan, M. Leitch, C. Xu*. 2013. Hydrothermal liquefaction of barks into bio-crude—Effects of species and ash content/composition. Fuel 116: 214-220.
Demirbas "Mechanisms of Thermal Degradation of Wood in Alkaline Glycerol". Energy Sources, Part A: Recovery, Utilization, and Environmental Effects, 2009 vol. 31:14, pp. 1294-1299.
Demirbas,A. "Liquefaction of Biomass Using Glycerol". Energy Sources, Part A: Recovery, Utilization, and Environmental Effects, 2008 vol. 30:12, pp. 1120-1126.
Demirbas, A. "Direct and Alkaline GlycerolLiquefaction of Haszelnut Shell", Energy Sources. Part A: Recovery, Utilization, and Environmental Effects, 2010, vol. 32:8, pp. 689-696.
International Search Report of the parent application PCT/CA2017/050774 dated Oct. 12, 2017.

* cited by examiner

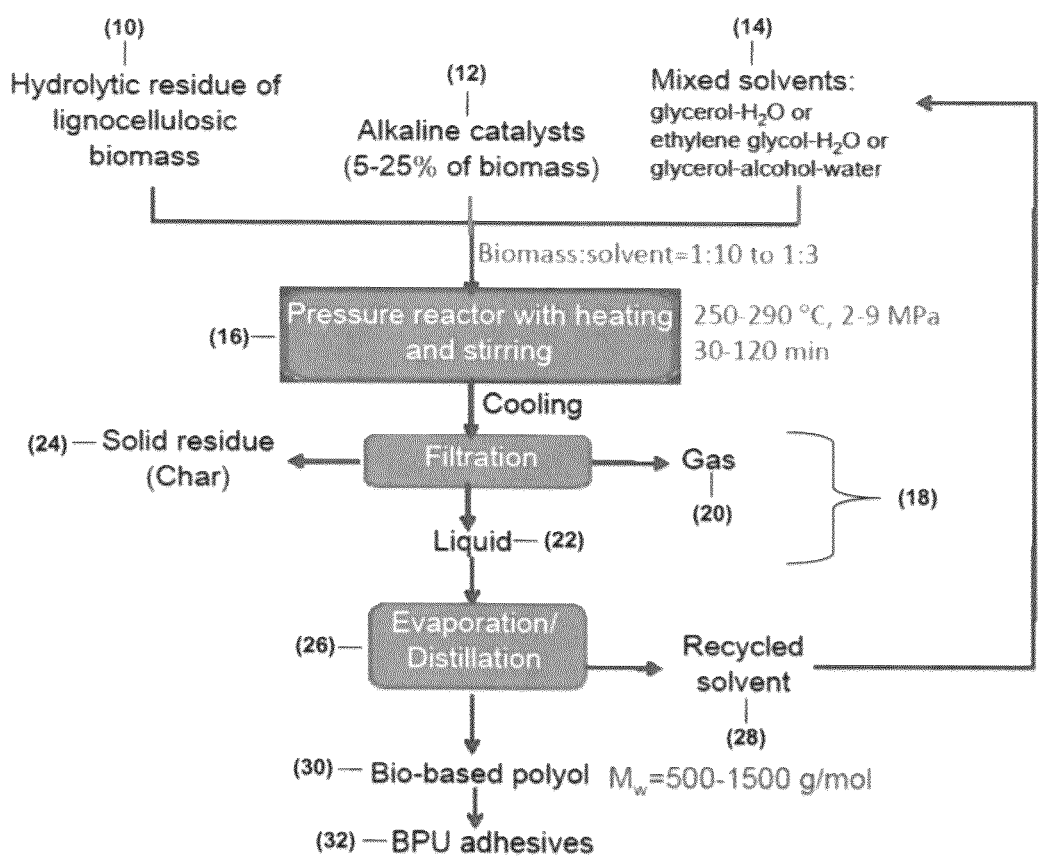
Liquefaction process

HYDROTHERMAL LIQUEFACTION OF LIGNOCELLULOSIC BIOMASS TO BIO-OILS WITH CONTROLLED MOLECULAR WEIGHTS

FIELD

The present disclosure relates to a highly efficient hydrothermal liquefaction process to produce bio-oils with controlled molecular weights from lignocellulosic biomass or municipal solid waste for applications as bio-polyols or bio-phenols in the production of various bio-based materials.

BACKGROUND

The declining fossil reserves, especially petroleum reserves and increasing concerns over greenhouse gas emissions and climate change have intensified the worldwide efforts in seeking alternative sources to fossil resources for energy, chemical and material production. The abundant agriculture and forestry biomass could be an ideal renewable carbon neutral alternative to fossil resources for the production energy and chemicals to safeguard future sustainable development of the world economics.

To date the most successful utilization of biomass is biochemical conversion of carbohydrates in biomass to alcohol through enzymatic hydrolysis-fermentation process. However, this method left over lignin and part of carbohydrates un-utilized as hydrolysis residues or waste materials. Over the last 20 years, much attention in biomass utilization has been focused on the thermal chemical conversion of biomass to bio-oil for fuel application through pyrolysis (thermal cracking of biomass in an inert atmosphere at a temperature over 400° C. under atmospheric or reduced pressure) and liquefaction (solvolytic degradation of biomass in a solvent under elevated pressure of 5-20 MPa at a low or medium temperature 250-400° C.) (Huber et al., 2006; Peterson et al., 2008; Brand et al., 2014). Bio-oils can be upgraded to liquid transportation bio-fuels via hydroprocessing (expensive though), and more promisingly utilized directly as bio-based chemicals for the production of high-value bio-based materials such as bio-based plastics and polymers.

Solvolytic liquefaction is a promising technique for conversion of biomass (in particular wet or high water-containing biomass) into low molecular weight bio-oil or bio-crude with greater heating value up to 30-40 MJ/kg, close to petroleum. Basic reaction pathways for the liquefaction of biomass can be described as: (i) dissociation of the three major components lignin, hemicellulose, and cellulose by heat and the solvent, (ii) depolymerization of the three major components into oligomers via hydrolytic/reductive/oxidative/cracking reactions; (iii) further decomposition of oligomers to monomer by cleavage reactions, (iv) rearrangement of light fragments through condensation, dehydration, cyclization and re-polymerization, leading to new compounds (Zhang et al., 2010; Toor et al., 2011; Demirbas, 2000 and 2011).

Reaction temperature, catalysts, solvent, and reaction time are the main factors that affect the yields and properties of the biomass liquefaction products (bio-oil, char and water soluble product and gases). For more efficient utilization of biomass, the yield of bio-oil shall be maximized and the yields of other products should be minimized.

For biofuel production, the bio-oil should have a molecular weight as low as possible. This can usually be accomplished by operation with a cracking catalyst at a higher temperature, in which condition gas formation would be much higher and the process become costly due to the use of expensive cracking catalyst and the high operating temperature.

For bio-based material applications, the bio-oil product can be of a mid-molecular weight, ideally around 1,000 g/mol according to the inventors' experience, achievable in a proper solvent with or without catalyst at a mild temperature. Effect of catalysts, solvent, temperature, and types of biomass on the yields and properties of the liquefaction products are still under investigation (Liu and Zhang, 2008; Karagoz et al., 2005).

Water has been very commonly used as an effective and green solvent for direct liquefaction of biomass in water, widely called hydrothermal liquefaction (HTL) of biomass (Peterson et al., 2008; Toor et al., 2011; Tekin et al., 2014a and 2014b; Kang et al., 2013).

The effects of process parameters on the HTL of biomass has been widely reviewed by Akhtar and Admin (2011) and Behrendt et al. (2008). HTL of agricultural and food processing wastes, agriculture residues and marine biomass, organic wastes and byproducts has been investigated by different groups (Yeh et al., 2013; Tekin and Karagoz, 2013; Pavlovic et al., 2013; Ruiz et al., 2013; Knez et al., 2015).

In the past years, the inventors' own group have been successful in liquefaction of woody biomass (sawdust, bark, peat, pulp/paper waste water sludge, etc.) into bio-crude at high yields up to 65 wt % in hot-compressed water, alcohols and alcohol-water mixture with or without a catalyst (KOH, NaOH, $Ca(OH)_2$, $K_2CO_3$, $FeSO_4$, iron oxide, etc.) at 300-400° C. and 10-25 MPa (Xu and Lad, 2007; Xu and Etcheverry, 2008; Xu and Lancaster, 2008; Yang et al., 2009; Li et al., 2011, Zhang et al., 2011; Feng et al., 2013).

The main drawback of liquefaction of biomass in water medium as well as some other low boiling point solvents such as methanol, ethanol and acetone, etc. is the high operation pressure, leading to a high capital cost and safety issues associated with the high operation pressure.

However, a process with severe operation conditions such as high operating temperature (over 300° C.) and high operating pressure (over 10 MPa) would limit its industrial application due to the associated high capital and operation costs.

Therefore, it would be desirable to implement a hydrothermal liquefaction process that converts the hydrolysis residues of lignocellulosic biomass into useable low-$M_w$ bio-oils under mild operation conditions, (<300° C. and <10 MPa), and at a high efficiency.

SUMMARY

The present disclosure describes a highly efficient hydrothermal liquefaction process for the production of controlled molecular weight ($M_w$) bio-oils, intended for use as bio-polyols or bio-phenols in the production of bio-based materials. The disclosed process is a less costly and more efficient method of producing the bio-oils required for the production of said bio-based materials. Bio-oil percent yield falls between 60-80%, with total biomass conversion being greater than 95%.

It is advantageous to use bio-oils of low $M_w$ (<<$1000_{g/mol}$), and moderate $M_w$ (~$1000_{g/mol}$) for the production of biofuels and bio-based materials, respectively. Molecular weights on this order can be controlled and achieved directly with the disclosed process, under mild operating conditions, yielding an oil product of moderate $M_w$ at lower cost and higher efficiency, or alternatively under severe operating conditions at a higher temperature, yielding an oil product of low $M_w$ for bio-fuel application at a higher cost admittedly.

In a given embodiment of the disclosed process, the reactants are comprised of the hydrolysis residue of lignocellulosic biomass and an alkaline catalyst in a mixed solvent (e.g. water, glycerol, and/or alcohol compounds to increase boil point and reduce operating pressure). The biomass to solvent ratio may be between 1:3 and 1:10.

The reactants are then converted to gas, liquid and solid phases in a pressure reactor under mild operating conditions, 250 to 290° C. and 2 to 9 MPa, for 30 to 120 minutes. The liquid phase is further separated into low/moderate molecular weight bio-oils (for use as bio-polyols or bio-phenols in biofuel/bio-based material production), and solvent, which is recycled back to the reactant mixture.

In an embodiment there is provided a hydrothermal liquefaction process for the synthesis of bio-oils with controlled molecular weights, comprising:

producing a reactant mixture by mixing any one or combination of the hydrolysis residue of lignocellulosic biomass, original lignocellulosic biomass, and municipal solid waste with an alkaline catalyst in a mixed solvent, said mixed solvent being any one or combination of glycerol-water, ethylene-glycol-water, glycerol-alcohol-water, or ethylene-glycol-alcohol-water, said reactant mixture having a solids to mixed solvent ratio in a range from about 1:3 to about 1:10 (w/w), and wherein said catalyst is present in an amount from about 5 wt % to about 30 wt % of the solids in the reactant mixture;

reacting, under pressure and heating, the reactant mixture under controlled conditions of temperature, pressure, and duration; cooling, filtering, and separating the reacted products into gas products, liquid products, and solid residue; and evaporating and distilling the liquid products to isolate bio-oils of desired molecular weight, and solvents.

A further understanding of the functional and advantageous aspects of the present disclosure can be realized by reference to the following detailed description and drawings.

BRIEF DESCRIPTION OF THE DRAWINGS

Embodiments disclosed herein will be fully understood from the following detailed description thereof taken in connection with the accompanying drawings, which form a part of this application, and in which:

FIG. 1 shows a detailed block diagram of the disclosed process.

DETAILED DESCRIPTION

Various embodiments and aspects of the disclosure will be described with reference to details discussed below. The following description and drawings are illustrative of the disclosure and are not to be construed as limiting the disclosure. Numerous specific details are described to provide a thorough understanding of various embodiments of the present disclosure. However, in certain instances, well-known or conventional details are not described in order to provide a concise discussion of embodiments of the present disclosure.

As used herein, the terms "comprises" and "comprising" are to be construed as being inclusive and open ended, and not exclusive. Specifically, when used in the specification and claims, the terms "comprises" and "comprising" and variations thereof mean the specified features, steps or components are included. These terms are not to be interpreted to exclude the presence of other features, steps or components.

As used herein, the term "exemplary" means "serving as an example, instance, or illustration," and should not be construed as preferred or advantageous over other configurations disclosed herein.

As used herein, the terms "about" and "approximately" are meant to cover variations that may exist in the upper and lower limits of the ranges of values, such as variations in properties, parameters, and dimensions.

For the bio-oils produced by the present process, a broad molecular weight range of the product bio-oils is in the range from about 500 g/mol to about 2500 g/mol.

A more preferred range is from about 600 g/mol to about 1500 g/mol.

As used herein, the terms "narrow molecular weight distribution" refer to a polydispersity index value in a range from 1 to about 5, but more preferably in a range from 1.5 to about 3.

The process disclosed herein provides a hydrothermal liquefaction process for the synthesis of bio-oils with controlled molecular weights which includes producing a reactant mixture by mixing the hydrolysis residue of lignocellulosic biomass, original lignocellulosic biomass or municipal solid waste with an alkaline catalyst in a mixed solvent. The original lignocellulosic biomass may be any one or combination of crop residues, forest biomass and forestry residues, and the hydrolysis residue of lignocellulosic biomass may be hydrolysis residue of any one or combination of crop residues, forest biomass and forestry residues.

The mixed solvent may be any one or combination of glycerol-water, ethylene-glycol-water, glycerol-alcohol-water, or ethylene-glycol-alcohol-water, the reactant mixture having a solids to mixed solvent ratio in a range from about 1:3 to about 1:10 (w/w), and in other embodiments it may be from about 1:3 to about 1:6 (w/w). The catalyst is present in an amount from about 5 wt % to about 30 wt % of the solids in the reactant mixture, and more preferably it is present in an amount from about 5 to about 15 wt %.

The reactant mixture is reacted under controlled conditions of temperature, pressure, and duration, and after a preselected amount of time the contents of the reactor are cooled, filtered, and then the reacted products are separated into gas products, liquid products, and solid residue. The liquid products are subject to evaporation and distillation to isolate bio-oils of desired molecular weight, and solvents.

The reactant mixture is reacted in a pressure reactor with reactor operating conditions such that the temperatures may be in a broad range from about 200° C. to about 350° C. but more preferably in the range from about 250° C. to about 290° C., the pressure may be in a broad range from about 1 MPa to about 20 MPa, and more preferably in the range from about 2 MPa to about 10 MPa. A more preferred pressure range is from about 4 to about 10 MPa. The duration of the reaction is between about 30 minutes to about 120 minutes.

It will be appreciated that the temperature and pressure the reactor is operated at will depend on the nature of the reactant mixture. For example, the lower the contents of low boiling point solvent, the higher the pressure at the same temperature.

The alkaline catalyst is any one or combination of NaOH, KOH, $Na_2CO_3$, $K_2CO_3$ CaO, $Ca(OH)_2$, and $Ba(OH)_2$. NaOH by its self exhibits excellent efficacy.

The yield of bio-oils show a percent yield between about 60% to about 80%, and results in a total biomass conversion greater than 95%.

The reaction conditions allow control over the molecular weights of the bio-oils and they can be controlled to be within the range of about $500_{g/mol}$ to about $2500_{g/mol}$, and are of narrow molecular weight distribution.

The leftover solvent for use in the reactant mixture may be recirculated back to the next batch thereby providing an economic advantage.

The synthesized bio oils are polyols and these may be used for producing biofuels and bio-polyurethane resins, adhesives, and foams as well as bio-phenol-formaldehyde resins/adhesives through the present process of hydrothermal liquefaction.

The present process will now be illustrating using the following non-limiting examples.

EXAMPLES

Materials and Methods

Residue from hydrolytic ethanol plant (hydrolysis residue) was used as the raw material for the experiments, which contains approximately 50-60 wt % lignin with remains being carbohydrates. Reagent grade glycerol, ethylene glycol, and acetone, ethanol and methanol as well as HPLC grade tetrahydrofuran were purchased from Caledon Chemical. Sodium hydroxide and sulfuric acid were purchased from Sigma-Aldrich.

The relative molecular weights of the liquid products were measured with a Waters Breeze GPC-HPLC (gel permeation chromatography-high performance liquid chromatography) instrument (1525 binary pump, UV detector at 270 nm; Waters Styrylgel HR1 column at a column temperature of 40° C.) using tetrahydrofuran (THF) as the eluent at a flow rate of 1 mL/min and linear polystyrene standards for molecular weight calibration.

Details of the results are presented in the following examples, additionally illustrated in the flow diagram in FIG. 1.

Example 1

Liquefaction of Hydrolysis Residue of Wood in Mixtures of Three Solvents 10 g Hydrolysis residue, shown at 10 (in FIG. 1), 40 mL Gly/MeOH/H$_2$O (45/45/10 volume/volume/volume, referred to herein as v/v/v, and shown at 14) co-solvent, and 1 g NaOH (10% weight with respect to mass of the biomass, shown at 12) were added in a 100 mL Parr pressure reactor, 16. The reactor was purged with N$_2$. After leakage check, the reactor was pressurized with 2 megapascal (MPa) N$_2$ and heated at 5-10° C./minutes (min) up to 290° C. under stirring (300 revolutions per minute (rpm)), remained at the temperature for reaction until the specified reaction time was elapsed. The reaction was quenched by cooling with a water bath. The reaction mixture, components shown at 18 in FIG. 1 was collected by washing with MeOH, filtered to obtain the solid residue (SR, shown at 24) and a bio-oil/solvent solution 22. A liquor of bio-oil solution was taken and precipitated to water at 26. The precipitated solid (i.e., bio-oil, 30) was dried for GPC measurement. The low boiling point solvent (methanol, ethanol, acetone, water, etc.) was removed from the filtrate by rotary evaporation at 50° C. under reduced pressure at 20. Bio-oil yield was calculated by the following Equation (1) below:

Bio-oil yield(wt %)=(Wt. of bio-oil containing high boiling-point solvent−Wt. of the high boiling-point solvent)/(Wt. dry biomass)×100%        Equation (1)

Further distillation of the liquid products under high vacuum can remove and recover high boiling point solvents such as glycerol.

The liquefaction of hydrolysis residue of wood in mixtures of three solvents at different reaction conditions were conducted and the results are presented in Table 1.

TABLE 1

Results from liquefaction of hydrolysis residue of wood in mixtures of three solvents.

| Solvent | | NaOH | T | P | Time | Yield (wt %) | | M$_w$ | |
|---|---|---|---|---|---|---|---|---|---|
| Name | Ratio (v/v/v) | (g) | (° C.) | (MPa) | (min) | Bio-oil | SR | (g/mol) | PDI |
| Gly/MeOH/H$_2$O | 45/45/10 | 0 | 290 | 7.0 | 60 | 46.9 | 2.2 | 920 | 2.00 |
| Gly/MeOH/H$_2$O | 45/45/10 | 1.00 | 290 | 7.3 | 60 | 70.0 | 3.22 | 990 | 1.96 |
| Gly/MeOH/H$_2$O | 45/45/10 | 1.00 | 290 | 7.3 | 30 | 61.3 | 10.6 | 950 | 1.70 |
| Gly/MeOH/H$_2$O | 45/45/10 | 1.00 | 260 | 7.3 | 60 | 62.5 | 8.5 | 980 | 1.85 |
| Gly/MeOH/H$_2$O | 45/45/10 | 0.50 | 290 | 7.3 | 60 | 61.4 | 7.5 | 1000 | 1.92 |
| Gly/EtOH/H$_2$O | 45/45/10 | 1.00 | 290 | 4.7 | 60 | 69.4 | 1.96 | 990 | 1.75 |

Gly = glycerol,
SR = solid residue

Example 2

The Liquefaction of Hydrolysis Residue of Wood in Mixtures of Two Solvents 10 g Hydrolysis residue, shown at 10 (FIG. 1), 40 mL Gly/H$_2$O (90/10, v/v, shown at 14) co-solvent, and 1 g NaOH (10% weight with respect to mass of the biomass) or 0.125 g H$_2$SO$_4$ as a comparison (shown at 12) were added in a 100 mL Parr pressure reactor, at 16. The reactor was purged with N$_2$. After leakage check, the reactor was pressurized with 2 MPa N$_2$ and heated at 5-10° C./min up to 290° C. under stirring (300 rpm), remained at the temperature for reaction until the specified reaction time was elapsed. The reaction was quenched with a water bath. The reaction mixture 18 was collected by washing with MeOH, filtered to obtain the solid residue (SR, 24) and a bio-oil/solvent solution, 22. A liquor of bio-oil solution was taken and precipitated to water at 26. The precipitated solid (i.e., bio-oil, 30) was dried for GPC measurement. The low boiling point solvent (methanol, ethanol, acetone, water, etc.) was removed from the filtrate by rotary evaporation at 50° C. under reduced pressure, shown at 20. Bio-oil yield was calculated by Equation (1) as described previously. Further distillation of the liquid products under high vacuum can remove and recover high boiling point solvent such as glycerol. The results in two solvents are shown in Table 2.

TABLE 2

Results from liquefaction of hydrolysis residue of wood in mixtures of two solvents.

| Solvent | | Catalyst | | T | P | Time | Yield (wt %) | | $M_w$ | |
|---|---|---|---|---|---|---|---|---|---|---|
| Name | Ratio (v/v/v) | Comp. | (g) | (° C.) | (MPa) | (min) | Bio-oil | SR | (g/mol) | PDI |
| Gly/H$_2$O | 90/10 | NaOH | 1.00 | 290 | 2.5 | 60 | 70.5 | 2.24 | 950 | 1.74 |
| MeOH/H$_2$O | 90/10 | NaOH | 1.00 | 290 | 15.8 | 60 | 20.4 | 34.9 | 380 | 1.65 |
| AcOH/H$_2$O | 80/20 | H$_2$SO$_4$ | 0.125 | 250 | 3.0 | 60 | 41.1 | 26.1 | 1800 | 2.77 |
| EtOH/H$_2$O | 50/50 | HCO$_2$h | 3.00 | 250 | 6.2 | 60 | 58.1 | 6.80 | 980 | 1.75 |
| EtOH/H$_2$O | 50/50 | H$_2$SO$_4$ | 0.125 | 250 | 6.2 | 30 | 54.3 | 13.7 | 1700 | 2.27 |

Gly = glycerol,
SR = solid residue

Example 3

Liquefaction of Hydrolysis Residue of Wood in Mono Solvents 10 g Hydrolysis residue, shown at 10 (FIG. 1), 40 mL glycerol at 14, and 1 g NaOH (10% weight with respect to mass of the biomass, shown at 12) were added in a 100 mL Parr pressure reactor at 16. The reactor was purged with N$_2$. After leakage check, the reactor was pressurized with 2 MPa N$_2$ and heated at 5-10° C./min up to 290° C. under stirring (300 rpm), remained at the temperature for reaction until the specified reaction time was elapsed. The reaction was quenched with a water bath. The reaction mixture 18 was collected by washing with MeOH, filtered to obtain the solid residue (SR, 24) and a bio-oil/solvent solution 22. A liquor of bio-oil solution was taken and precipitated to water at 26. The precipitated solid (i.e., bio-oil, 30) was dried for GPC measurement. The low boiling point solvent (methanol, ethanol, acetone, water, etc.) was removed from the filtrate by rotary evaporation at 50° C. under reduced pressure, shown at 20. Bio-oil yield was calculated by Eq. (1) as described previously. Further distillation of the liquid products under high vacuum can remove and recover high boiling point solvent such as glycerol. The results in mono solvents are shown in Table 3.

TABLE 3

Results from liquefaction of hydrolysis residue of wood in mono solvents.

| | Solvent | P | Yield (wt %) | | | | |
|---|---|---|---|---|---|---|---|
| Feedstock | Name | (MPa) | Bio-oil | SR | $M_n$ | $M_w$ | PDI |
| Hydrolysis residue of wood | Glycerol | 2.4 | 70.4 | 1.6 | 440 | 770 | 1.75 |
| | MeOH | 16.9 | 32.3 | 37.0 | 230 | 380 | 1.65 |
| | H$_2$O | 7.2 | 68.7 | 21.2 | 360 | 640 | 1.78 |

Catalyst: 1.00 g NaOH (10 wt % of biomass), reaction temperature: 290° C., reaction time: 1 h.

Results and Discussion

The developed process works for direct liquefaction of hydrolysis residue of lignocellulosic biomass 10 (FIG. 1), under mild conditions (<300° C. and <10 MPa), employing inexpensive alkali compounds 12 as catalysts (NaOH or KOH or Na$_2$CO$_3$ or K$_2$CO$_3$, etc.). It employs mixed alcohol-water solvents, e.g., glycerol-methanol (or ethanol)-water or glycerol-water, 14, where all solvents are recyclable and reusable (as shown at 28), resulting in very high biomass conversion (>95%) and a bio-oil yield (~70 wt %). The produced bio-oil 30 has a very low molecular weight ($M_w$<1000 g/mol) and much narrow molecular weight distribution (PDI<2). The low-$M_w$ bio-oils from hydrolysis residue of lignocellulosic biomass can be utilized as a liquid bio-fuel or bio-based chemicals such as bio-polyols for the production of bio-based materials (e.g., polyurethane resins/adhesives/foams, 32).

Under the typical conditions (i.e., 290° C., 1 h reaction time, 20 wt. % biomass substrate concentration, NaOH catalyst addition at 10 wt % of the substrate) using glycerol-water co-solvent (90/10 v/v), the maximum reactor pressure observed was 2.5 MPa, biomass conversion and bio-oil yield achieved were ~98% and ~71%, respectively, and the bio-oil product has a number-average molecular weight ($M_n$) of 540 g/mol and a weight-average molecular weight ($M_w$) of 950 g/mol. Under the same conditions but using glycerol-methanol-water co-solvent (45/45/10 v/v/v), the maximum reactor pressure observed was 7.3 MPa, biomass conversion and bio-oil yield achieved were ~97% and ~70%, respectively, and the bio-oil product has an $M_n$ of 510 g/mol and $M_w$ of 990 g/mol.

Effects of Catalyst

As the main chemical reactions in liquefaction is the hydrolysis of ether bonds among cellulose, hemicellulose, and lignin, both acid and base can catalyze the reaction. The ether bonds are more easily susceptible to acid attack. The liquefaction without catalyst in water or ethanol/water is actually an accelerated acid self-catalyzed reaction because acid can be produced in the course of the reaction as it was found the finally pH value significantly decreased from 7 before liquefaction to 1-2 after liquefaction. The reaction usually took 0.5-1 hour (h) at 250-300° C. (Feng, etc., 2013). When 1-1.5 wt. % (based on biomass) H$_2$SO$_4$ was used, the reaction only took 15-30 min. A drawback of strong acid of catalyst is it catalyzes re-polymerization or condensation reactions, so the molecular weight of the final bio-oil product is much higher (1800 g/mol vs 1000 g/mol).

Bases as catalysts for liquefaction are not well investigated. A comparison of the results from Tables 1-4 show that when NaOH was used as a catalyst in mixed glycerol solvent, a 60 min reaction of hydrolysis residue of wood produced bio-oil at a high and stable yield of 70%, and solid residue at a very low yield (around 2-3%). In alkaline condition, the condensation/re-polymerization reaction was prohibited. The bio-oil products have relatively lower molecular weight (1000 g/mol) and narrow molecular distribution. The molecular weight range makes the bio-oil product a good candidate for material synthesis, especially for polyurethane, epoxy resin and phenol-formaldehyde resin.

Different amounts of catalyst were tested. It was found a lower product yield was obtained at a lower addition amount of NaOH. Further increasing NaOH addition amount would increase the bio-oil product yield, however would also increase the reagent and work-up (need to neutralize NaOH) costs. Thus, 10 wt % of NaOH was considered to be the optimal amount.

Effects of Solvents

Liquefaction of biomass in water/ethanol low boiling point solvent was widely tested. The major drawback with low boiling point solvent is the high operation pressure, (over 12 MPa) which would create safety issues and increase investment. When high boiling point polyols (i.e., glycerol) were used, the operation pressure was significantly reduced to below 7.5 MPa. Glycerol has better solubility for biomass, as can be seen in Table 2 for mixed two component solvents, glycerol/$H_2O$ gave much higher bio-oil yield and lower SR yield than EtOH/$H_2O$ and MeOH/$H_2O$ at the same reaction condition. Glycerol is therefore a better solvent for the liquefaction of hydrolysis residue of lignocellulosic biomass.

Effects of Temperature

The liquefaction of biomass at alkaline condition usually requires a higher temperature than that at acidic condition. From Table 1, one can observe that the bio-oil product yield was much lower, accompanied by a higher SR yield at 260° C. than those at 290° C. using a glycerol solvent mixture. Further increasing reaction temperature will increase the energy cost, so 290° C. can be chosen as the optimal temperature for this process.

Effects of Reaction Time

From Table 1, the product yield was much lower, accompanied by a much higher SR in the operation for 0.5 h than that for 1 h using a glycerol solvent mixture. Since further increasing reaction time is not economically beneficial, the optimal reaction time can be chosen to be 1 h.

The present process can achieve very high biomass conversion (>95%) with a bio-oil yield of ~70 wt %. The process is very advantageous in that the produced bio-oil has a very low molecular weight ($M_w$<1000 g/mol) and much uniform molecular weight distribution (PDI<2). Under the typical conditions (i.e., 290° C., 1 h reaction time, 20 wt. % biomass (hydrolysis lignin) substrate concentration, NaOH catalyst addition at 10 wt % of the substrate) using glycerol-water co-solvent (90/10 v/v), the maximum reactor pressure observed was 25 bar, biomass conversion and bio-oil yield achieved were ~98% and ~71%, respectively, and the bio-oil product has a number-average molecular weight ($M_n$) of 540 g/mol and a weight-average molecular weight ($M_w$) of 950 g/mol. Under the same conditions but using glycerol-methanol-water co-solvent (45/45/10 v/v/v), the maximum reactor pressure observed was 73 bar, biomass conversion and bio-oil yield achieved were ~97% and ~70%, respectively, and the bio-oil product has an $M_n$ of 510 g/mol and $M_w$ of 990 g/mol.

The present method employs mixed alcohol-water solvents, e.g., glycerol-methanol (or ethanol)-water or glycerol-water, and all solvents are recyclable and reusable.

The synthesized bio oils can be used as biobased liquid polyols directly or via oxypropylation. As an example, for synthesis of biobased liquid polyols with 50% bio-content via oxypropylation, 20 parts of DHL, 20 parts Propylene oxide (PO), 0.50 part of KOH with 15.0 parts of acetone were used. After all ingredients were loaded in the reactor and leak check was conducted. The reactor was then heated to 150° C. and allowed reaction for 2 h until no more pressure drop. After reaction, the reactor was cooled to room temperature. Oxypropylated sample was transferred from reactor to a flask, neutralized with phosphoric acid, filtered. The solvent and any unreacted PO were removed by rotary evaporation under vacuum to remove acetone. The final weight of oxypropylated sample was exactly equal to sum of input bio oil and PO input.

The bio-based polyols can then be utilized for the production of formaldehyde free bio-based polyurethane (BPU) resins/adhesives by mixing with polyisocyanates (such as TDI and MDI) at about 50/50 parts.

While the teachings described herein are in conjunction with various embodiments for illustrative purposes, it is not intended that these teachings be limited to such embodiments. On the contrary, the teachings described and illustrated herein encompass various alternatives, modifications, and equivalents, without departing from the embodiments, the general scope of which is defined in the appended claims.

Except to the extent necessary or inherent in the processes themselves, no particular order or steps or stages of methods or processes described in this disclosure is intended or implied. In many cases the order of process steps may be varied without changing the purpose, effect, or import of the methods described.

What is claimed is:

1. A hydrothermal liquefaction process for the synthesis of bio-oils with weight-average molecular weights in the range of about 500 g/mol to about 2500 g/mol from lignocellulosic biomass, comprising:

producing a reactant mixture by mixing any one or combination of the hydrolysis residue of lignocellulosic biomass, and original lignocellulosic biomass with an alkaline catalyst in a glycerol-water based mixed solvent, said mixed solvent being any one or combination of glycerol-water, or glycerol-alcohol-water, said reactant mixture having a solids to mixed solvent ratio in a range from about 1:3 to about 1:10 (w/w), and wherein said catalyst is present in an amount from about 5 wt % to about 30 wt % of the solids in the reactant mixture;

reacting, and heating the reactant mixture; cooling, filtering, and separating the reacted products into gas products, liquid products, and solid residue; and evaporating and distilling the liquid products to isolate bio-oils of weight-average molecular weight in the range of about 500 g/mol to about 2500 g/mol, and recover solvents.

2. The hydrothermal liquefaction process according to claim 1, wherein said reactant mixture reacts in a pressure reactor, wherein reactor operating conditions are about 200° C. to about 350° C. in temperature, about 1 MPa to about 15 MPa in pressure.

3. The hydrothermal liquefaction process according to claim 1, wherein said reactant mixture reacts in a pressure reactor, wherein reactor operating conditions are about 250° C. to about 290° C. in temperature, about 2 MPa to about 10 MPa in pressure and about 30 minutes to about 120 minutes in duration.

4. The hydrothermal liquefaction process according to claim 1, wherein said alkaline catalyst is any one or combination of: NaOH, KOH, $Na_2CO_3$, $K_2CO_3$, CaO, $Ca(OH)_2$, and $Ba(OH)_2$.

5. The hydrothermal liquefaction process according to claim 1, wherein reactor operating conditions are <300° C. in temperature, and <10 MPa in pressure, and said bio-oils show a percent yield between about 60% to about 80%, and results in a biomass conversion greater than 95%.

6. The hydrothermal liquefaction process according to claim 1, wherein the weight-average molecular weights of said bio-oils are within the range of about 600 g/mol to about 1500 g/mol.

7. The hydrothermal liquefaction process according to claim 1, wherein the weight-average molecular weights of said bio-oils are about 1000 g/mol.

8. The hydrothermal liquefaction process according to claim 1, wherein the bio-oils have a polydispersity index value in a range from 1 to about 5.

9. The hydrothermal liquefaction process according to claim 1, wherein the bio-oils have a polydispersity index value in a range from about 1.5 to about 3.

10. The hydrothermal liquefaction process according to claim 1, including a step of recycling leftover solvent for use in the reactant mixture.

11. The hydrothermal liquefaction process according to claim 1, wherein said catalyst is present in an amount from about 5 to about 15 wt % of said reactant biomass.

12. The hydrothermal liquefaction process according to claim 1, wherein said biomass to mixed solvent ratio is in a range from about 1:3 to about 1:6 (w/w).

13. The hydrothermal liquefaction process according to claim 1, wherein reactor operating pressure is in a range from about 1 to about 10 MPa.

14. The hydrothermal liquefaction process according to claim 1, wherein reactor operating pressure is in a range from about 2 to about 8 MPa.

15. The hydrothermal liquefaction process according to claim 1, wherein said produced bio oils are polyols or bio-phenols.

16. The hydrothermal liquefaction process according to claim 1, wherein said original lignocellulosic biomass is any one or combination of crop residues, forest biomass and forestry residues, and wherein the hydrolysis residue of lignocellulosic biomass is hydrolysis residue of any one or combination of crop residues, forest biomass and forestry residues.

17. The hydrothermal liquefaction process according to claim 1, wherein said reaction is carried out from about 30 minutes to about 120 minutes in duration.

18. Bio-oils obtained through the hydrothermal liquefaction process according to claim 1, for use as bio-crude for the production of biofuels, or as bio-polyols or bio-phenols for the synthesis of bio-polyurethane resins, adhesives, foams and bio-phenol-formaldehyde resins/adhesives, said bio-oils having weight-average molecular weights in the range of about 500 g/mol to about 2500 g/mol.

19. The Bio-oils according to claim 18, wherein the weight-average molecular weights are about 1000 g/mol.

20. The Bio-oils according to claim 18, wherein said glycerol-water based mixed solvent is glycerol-methanol-water at a volume ratio of 45:45:10, glycerol-ethanol-water at a volume ratio of 45:45:10, or glycerol-water at a volume ratio of 90:10.

21. The hydrothermal liquefaction process according to claim 1, wherein the weight-average molecular weights of said bio-oils are about 1000 g/mol.

22. The hydrothermal liquefaction process according to claim 1, wherein said glycerol-water based mixed solvent is glycerol-methanol-water at a volume ratio of 45:45:10, glycerol-ethanol-water at a volume ratio of 45:45:10, or glycerol-water at a volume ratio of 90:10.

* * * * *